United States Patent [19]
Walters

[11] 4,038,991
[45] Aug. 2, 1977

[54] CARDIAC PACER WITH RATE LIMITING MEANS

[75] Inventor: Robert A. Walters, Pittsburgh, Pa.

[73] Assignee: ARCO Medical Products Company, Leechburg, Pa.

[21] Appl. No.: 666,737

[22] Filed: Mar. 15, 1976

[51] Int. Cl.² ............................................. A61N 1/36
[52] U.S. Cl. ........................................... 128/419 PG
[58] Field of Search ........ 128/419 P, 419 PG, 419 PS, 128/419 R, 421, 422, 423

[56] References Cited

U.S. PATENT DOCUMENTS

| | | | |
|---|---|---|---|
| 3,311,111 | 3/1967 | Bowers | 128/419 PG |
| 3,557,796 | 1/1971 | Keller, Jr. et al. | 128/419 PG |
| 3,822,707 | 7/1974 | Adducci et al. | 128/419 PS |
| 3,833,005 | 9/1974 | Wingrove | 128/419 PG |
| 3,903,897 | 9/1975 | Woollons et al. | 128/419 PG |
| 3,920,024 | 11/1975 | Bowers | 128/419 PG |
| 3,926,198 | 12/1975 | Kolenick | 128/419 PG |
| 3,945,387 | 3/1976 | Adams | 128/419 PG |

*Primary Examiner*—William E. Kamm
*Attorney, Agent, or Firm*—John C. Martin, Jr.

[57] ABSTRACT

A cardiac pacer includes means connected to electrodes adapted to be connected to a patient's heart for detecting and amplifying naturally occurring heart pulses. First and second counters are provided to receive periodic pulses from a clock pulse generator to time a refractory period and a stimulation pulse period, respectively. A rate limiting circuit limits the stimulation pulse rate to a predetermined rate, above which, the pacer is precluded from producing stimulation pulses. A test circuit is selectively connectable to produce a visual indication of the production of a stimulation pulse.

2 Claims, 2 Drawing Figures

CARDIAC PACER WITH RATE LIMITING MEANS

BACKGROUND OF THE INVENTION

1. Field of the Invention

This invention relates to cardiac pacers, and more particularly, to cardiac pacers employing digital circuitry means for controlling the pacer operation.

2. Description of the Prior Art

Digital cardiac pacers have been described, most of which are intended for implantation into the body of the patient.

In so far as is known to applicant, none of the digital pacers heretofore advanced present means for providing an upper limit upon the stimulation pulse production rate which may occur as a result in the change in value of a critical pacer timing component. Additionally, especially in pacers which are primarily intended for external use, battery lifetime considerations are for the most part not considered, or at least are not of primary importance; consequently, most heart pacers of the prior art require frequent battery replacement.

What is needed is a pacer which can be employed externally to the patient, which can selectively provide an indication of its proper operation, which provides a circuit to prevent runaway of the pacer due to component drifts, and which is efficient in its power consumption requirements.

SUMMARY OF THE INVENTION

In light of the above, therefore, it is an object of the invention to provide a cardiac pacer for use external to a user's body.

It is another object of the invention to provide a cardiac pacer having rate limiting means to prevent the pacer from producing stimulation pulses above a preselected rate.

It is another object of the invention to provide a high efficiency digitally controlled external cardiac pacer.

It is yet another object of the invention to provide a heart pacer which has various selectible operating parameters.

It is still another object of the invention to provide a cardiac pacer which provides a visual indication of the generation of a stimulation pulse at the discretion of the operator.

It is another object of the invention to provide a cardiac pacer which includes a pair of associated digital counters to respectively provide a refractory period and stimulation pulse interval.

It is yet another object of the invention to provide a cardiac pacer which can be powered by low voltage batteries such as a lithium iodide cell, or the like, for relatively long battery life.

These and other objects, features, and advantages will become apparent to those skilled in the art from the following detailed description when read in conjunction with the accompanying drawings and appended claims.

The invention, in its broad aspect, presents a cardiac demand pacer for producing stimulation pulses for delivery to electrodes adapted to be connected to a heart to be stimulated. The pacer includes means connected to the electrodes for producing a signal indicating the presence of a heartbeat. An oscillator is provided for producing periodic pulses, and first and second pulse counter means are connected to the oscillator. The first pulse counter means counts a refractory period and the second pulse counter means counts a stimulation period. The first pulse counter means is reset by a heartbeat indicating signal, and produces a resetting signal upon being reset by the heartbeat indicating signal after the refractory period count to reset the second counter means. A stimulation pulse generator is also provided which is activated by the second counter means upon reaching the stimulation pulse period to deliver a stimulation pulse to the electrodes.

In another aspect of the invention, rate limiting means are provided to prevent the pacer from producing a stimulation pulse in the event the stimulation pulse rate exceeds a predetermined rate.

BRIEF DESCRIPTION OF THE DRAWING

The invention as illustrated in the accompanying drawing wherein.

DETAILED DESCRIPTION OF THE PREFERRED EMBODIMENTS

Figure 1A:
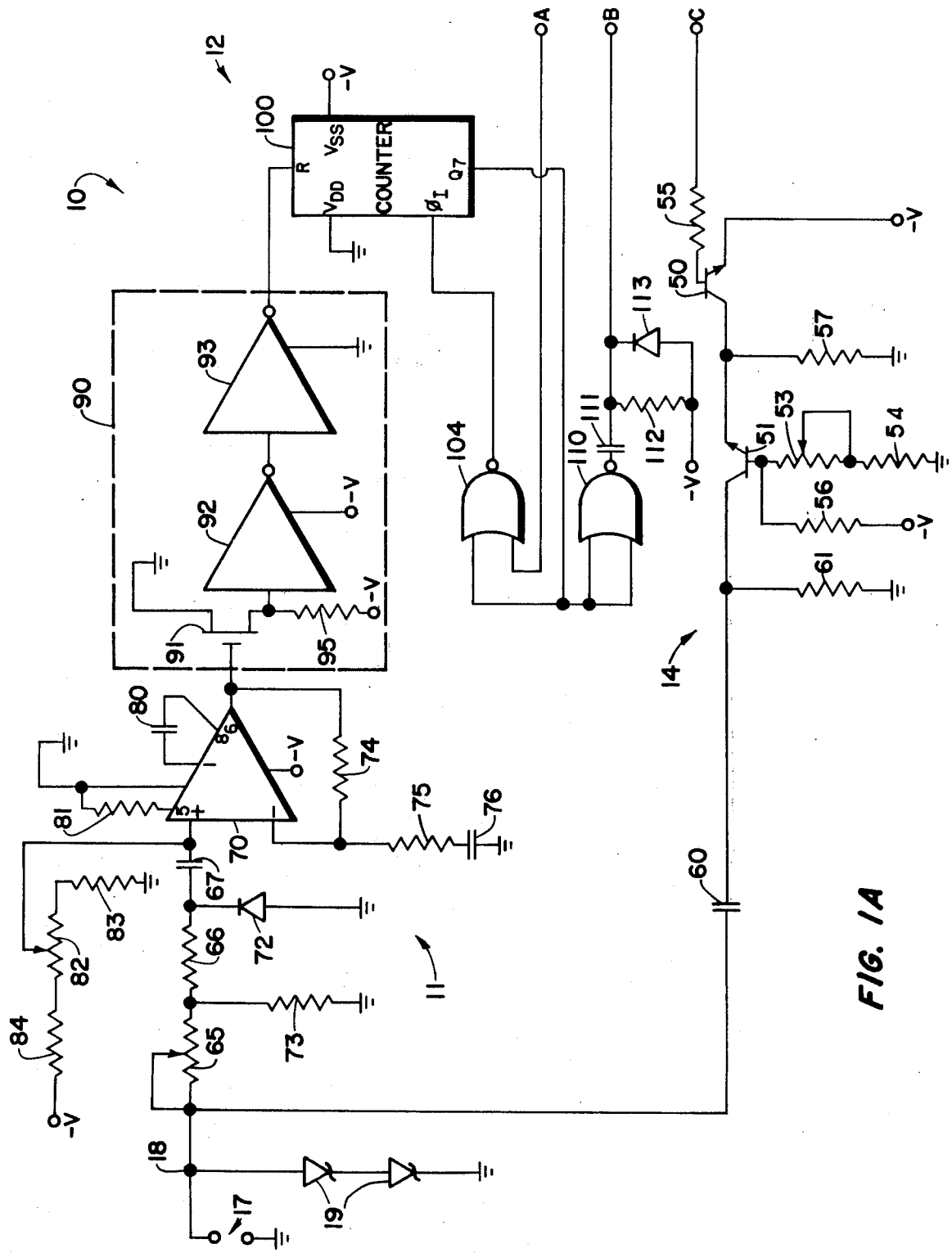
FIGS. 1A and 1B show an electrical schematic diagram of an external heart pacer in accordance with a preferred embodiment of the invention.
Figure 1B:
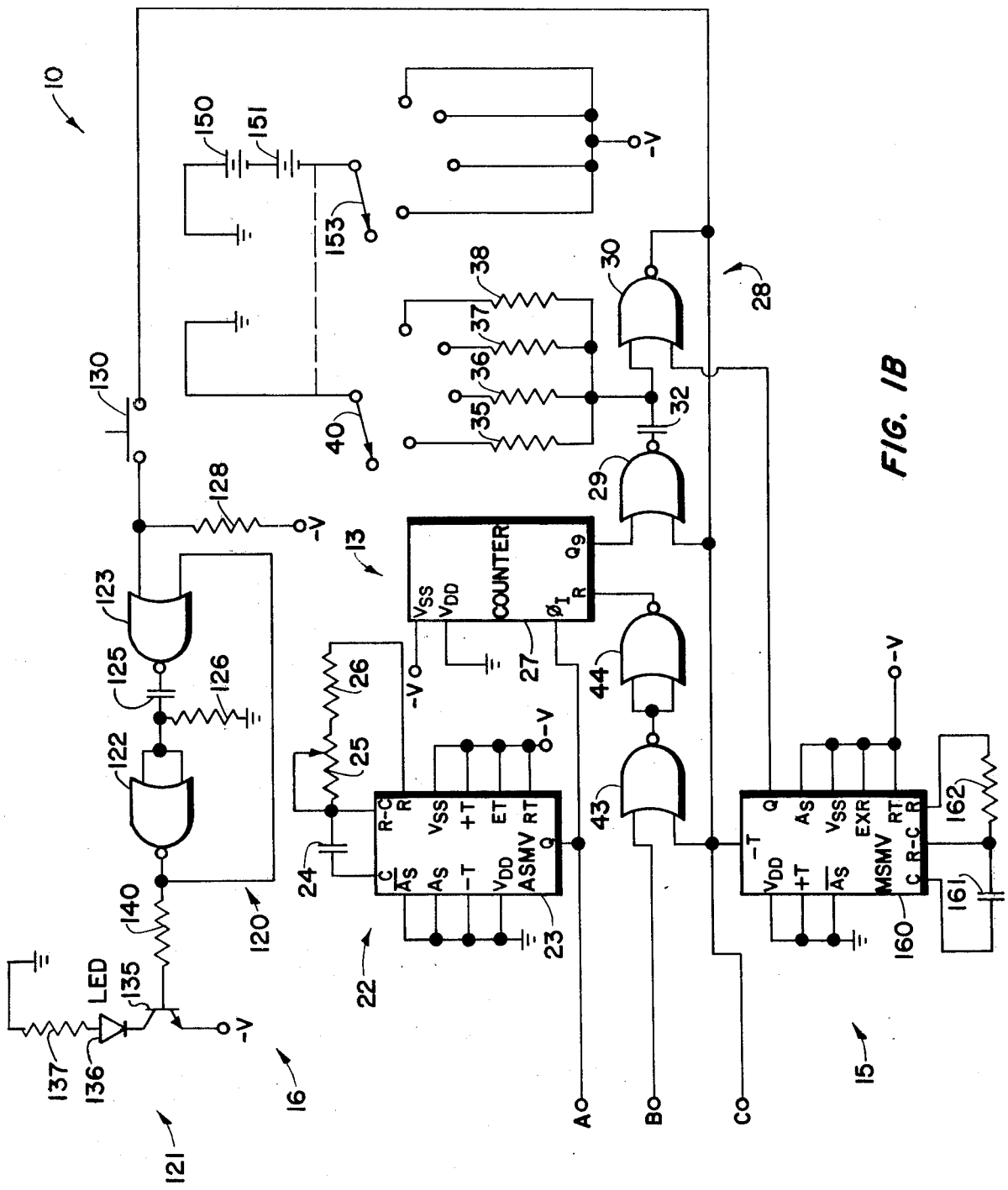

The external cardiac pacer of the invention is shown in FIGS. 1A and 1B, and is illustrated by the general reference numeral 10. The pacer includes six general circuits: an R-wave detector and amplifier circuit 11, a refractory period timer 12, a stimulation pulse interval timer 13, an output pulse amplifier 14, a rate limiting circuit 15 and a test circuit 16 for indicating the production of a stimulation pulse.

The pacer is designed for connection to electrodes (not shown) adapted to be connected to the user's heart, such electrodes, being known in the art, are not described herein in further detail. Terminals 17 are provided for such electrode connection. Thus, the cardiac pulses produced by the pacer 10 are conducted upon a line 18, connected to the terminal 17.

For the purpose of generating the stimulation pulses, a stimulation pulse timing circuit 13 is used. The timing circuit 13 includes a master oscillator circuit 22, which includes an astable multivibrator 23, the oscillation rate of which is controlled by a capacitor 24, a variable resistor 25, and a fixed resistor 26. The capacitor 24 is connected between the C and R-C inputs to the astable multivibrator 23, and the fixed resistor 26 and variable resistor 25 are connected in series between the R-C and R inputs. The output from the astable multivibrator 23 is taken from the Q output terminal thereof.

A counter 27 counts the pulses produced at the Q output of the astable multivibrator 23. The Q output of the astable multivibrator 23 is connected to the $\phi_I$ input of the counter 27, and the output of the counter 27 is derived at its $Q_9$ output terminal.

The manner of operation of the counter 27 is that it is advanced one step in binary order on the negative transition of $\phi_I$. Thus, the output state upon the output terminal $Q_9$ is controlled by the selection of the values of the capacitor 24 and resistors 25 and 26. The output upon the terminal $Q_9$ of the counter 27 is conducted to a "one shot" multivibrator circuit 28 which includes two NOR gates 29 and 30. The output of the NOR gate 29 is connected to the input terminals of the NOR gate 30 by a capacitor 32 and the output of the NOR gate 30 is connected to an input of the NOR gate 29 to provide a feedback path. The output terminal $Q_9$ of the counter 27 is connected to the other input of the NOR gate 29. Four resistors 35-38 are connected between the inputs of the NOR gate 30 and terminals of a switch 40 which is connected to ground. Thus, as will be recognized by those skilled in the art, the pulse width of the pulse produced at the output of the NOR gate 30 can be controlled by the selection of one of the resistors 35–38 by the switch 40. This selection capability provides a pulse width adjustment, as will be described below in detail.

The output of the NOR gate 30 is connected to the reset terminal of the counter 27 via a NOR gate 43 and an inverter connected NOR gate 44. Thus, when the state of the output upon the terminal $Q_9$ of the oscillator 27 changes from low to high states, the output from the NOR gate 30 changes from low to high states, thereby resetting the count of the counter 27. The period of the change in state on the output terminal $Q_9$, therefore, corresponds to the asynchronous rate of the cardiac pacer 10. The output of the NOR gate 30 is also conducted to the stimulation pulse amplifier 14 to produce a stimulation pulse for delivery upon line 18 to the heart electrodes at terminal 17, as presently described.

The stimulation pulse amplifier 14 includes two transistors 50 and 51. The emitter of the transistor 50 is connected to a negative terminal, and the collector is connected to the emitter of the transistor 51. A resistor 55 is connected between the output of the NOR gate 30 and the base of the transistor 50 to conduct the output pulse produced by the NOR gate 30 thereto to control the conduction thereof.

The collector of the transistor 51 is connected by a capacitor 60 to the output line 18. A variable resistor 53 is connected in series with a fixed resistor 54, the series being connected between the base of the transistor 51 and ground. The wiper arm of the variable resistor 53 is connected to the topside of the fixed resistor 54. A resistor 56 is connected from the base of the transistor 51 to a negative terminal, as shown, to bias the transistor 51 normally out of conduction. A resistor 57 is connected from the collector of the transistor 50 to ground, and a resistor 61 is connected from the collector of the transistor 51 to ground, to establish the bias conditions upon the respective transistors. The variable resistor 53 controls the emitter-base junction voltage to control the conduction through the transistor 51, hence the amplitude of the output pulse produced.

Thus, in operation, when a change in state is produced at the output of the NOR gate 30, the transistor 50 is biased into conduction, thereby providing a voltage drop across the resistor 57. The increasing negative potential developed is applied to the emitter of the transistor 51 to forward bias the emitter-base junction thereof to switch it on. Thus, a conduction path is established through the collector and emitter of the transistor 51 and the emitter and collector of the transistor 50 via the capacitor 60 to the output terminal 17. The degree to which the conduction path is established and therefore the amplitude of the output pulse is controlled by the variable resistor 53, which controls the emitter-base junction voltage of the transistor 51, as mentioned above.

The pulses upon line 18, i.e. the stimulation pulse produced by the amplifier 14 or the detected R-wave pulses, are conducted to the R-wave detector and amplifier 11 on line 18. A pair of Zener diodes 19 are connected in series between the line 18 and ground. The R-wave detector and amplifier 11, includes a variable resistor 65 connected in series with a resistor 66 which, in turn, in connected in series with a capacitor 67 to a non-inverting input of an operational amplifier 70. The capacitor 67 serves as a low frequency filter, rejecting signals upon the line 18 of undesirably low frequency. A diode 72 is connected between the junction of the resistor 66 and the capacitor 67 to establish a maximum voltage level which will be applied to the non-inverting input of the operational amplifier 70. A resistor 73 is connected between the junction of the variable resistor 65 and the resistor 66 to ground. The voltage applied to the non-inverting input of the operation amplifier 70 is controlled by the variable resistor 65, which, therefore, provides a sensitivity adjustment for the cardiac pacer 10 by adjusting the level of the input signal developed across the resistor 73.

A feedback resistor 74 is connected between the output of the operational amplifier 70 and its inverting input, and a resistor 75 connected in series with a capacitor 76 is connected between the non-inverting input of the operational amplifier 70 and ground. Thus, the voltage amplification of the operational amplifier 70 is determined by the sum of the impedances of the resistor 74 and the resistor 75 and capacitor 76 divided by the sum of the impedances of the resistor 75 and capacitor 76. It can therefore be seen that the capacitor 76 provides a high amplifier gain at higher frequencies and a lower amplifier gain at lower frequencies, and therefore provides the amplifier 70 with a low frequency filtering capability.

A small feed forward frequency compensating capacitor 80 is connected to the operational amplifier 70 in a manner well known in the art. A balancing resistor 81 is additionally provided connected between the amplifier 70 and ground. A variable resistor 82 is connected in series with a fixed resistors 83 and 84 between ground and a negative terminal, with the arm of the variable resistor 82 connected to the non-inverting input of the amplifier 70, to thereby provide means for balancing the offset voltage of the amplifier 70.

The output of the operational amplifier 70 is connected to an inverting circuit 90 which includes a MOSFET 91 and two inverters 92 and 93. The source and drain of the MOSFET 91 are connected between ground and a negative terminal, a load resistor 95 being provided in the drain circuit upon which the output voltage of the MOSFET 91 is developed. The input to the inverting circuit 90 is connected to the gate of the MOSFET 91. The signal developed across the resistor 95 is conducted via the inverters 92 and 93 to the refractory timing circuit 12, as next described.

The refractory timing circuit 12 includes a counter 100 which is reset by the signal developed at the output of the inverter 93. The output Q of the astable multivibrator 23 is conducted via a NOR gate 104 to the $\phi_I$ input of the counter 100. An output of the counter 100, for example, at the $Q_7$ terminal is conducted to the other input of the NOR gate 104, whereby the logic signal applied to the $\phi_I$ input is $\overline{Q_7} \cdot \overline{Q_{ASMV}}$. Thus, the counter 100 operates from a reset condition to a count at which the $Q_7$ output state changes from low at high states, at which time the output of the NOR gate 104 becomes low, thereby discontinuing the count by the counter 100.

The output terminal $Q_7$ is also connected to an inverter connected NOR gate 110, the output of which is conducted via a capacitor 111 to another input of the NOR gate 43 (FIG. 1B). A resistor 112 is connected between the other input of the NOR gate 43 and a negative terminal and a diode 113 is connected in parallel with the resistor 112 to establish a normally low state at the input to the NOR gate 43.

Thus, the refractory portion of the cardiac pacer circuit 10 operates as follows. When a signal appears upon the line 18, it is amplified by the operational amplifier 70 and is applied to the counter 100 to reset its count. Upon being reset, the output state at terminal $Q_7$ becomes low, thereby enabling the counter 100 to begin counting. When the state of the output upon the terminal $Q_7$ changes from low to high, the counter 100 is again disabled. Meanwhile, while the output state $Q_7$ is low, a low logic state is applied to the reset terminal of the counter 27, thereby enabling its count. When the state upon the output terminal $Q_7$ of the counter 100, however, changes from low to high, the output from the inverter 110 changes from high to low. Since the input to the NOR gate 43 was already low, no change is seen upon the reset terminal of the counter 27. Thereafter, however, if the counter 100 is reset by, for example, the reception of a naturally produced R-wave as detected by the R-wave detector circuit 11, the output state upon the terminal $Q_7$ will again change from high to low. This change will produce a change in the output of the inverter 110 from low to high which will charge the capacitor 111 to a high state. Thus, until the high state is discharged from the capacitor 111 by the resistor 112 to the negative terminal, the counter 27 will receive a high state upon its reset terminal, thereby resetting its count. Thus, it can be seen that if a resetting pulse is applied to the counter 100 prior to the time that the $Q_7$ state change is reached, no resetting pulse will be generated to reset the counter 27, thereby providing a refractory period nonresponsiveness to the counter 27. After the $Q_7$ state change is reached, however, a resetting pulse applied to the counter 100 will produce a resetting pulse to the counter 27, to thereby permit demand pacer operation.

The operation of the circuit can be monitored by the monitor circuit 16, which includes a one shot multivibrator circuit 120 and a light emitting diode (LED) controlling circuit 121. The one shot multivibrator circuit 120 includes two NOR gates 122 and 123, interconnected by a capacitor 125. A resistor 126 is connected from the input of the inverter-connected NOR gate 122 to ground, and the output of the NOR gate 122 is connected to an input of the NOR gate 123. A switch 130 is connected in series with the line from the output of the NOR gate 30 to the other input of the NOR gate 123, and a resistor 128 is connected from the NOR gate side of the switch 130 to a negative voltage.

A transistor 135 has its emitter connected to the negative terminal, and has the LED 136 and a resistor 137 connected in series between its collector and ground. A base resistor 140 is connected between the base of the transistor 135 and the output of the NOR gate 122. In operation of the monitor circuit 16, if the operation of the pacer circuit 10 is desired to be monitored, the test switch 130 is depressed. Upon the generation of a stimulation pulse by the one shot multivibrator circuit 28, a pulse is generated at the output of the NOR gate 122. The pulse at the output of the NOR gate 122 is applied to the base of the transistor 135 by the resistor 140 causing current to be conducted through the collector resistor 137 and light emitting diode 136, to indicate operation of the circuit 10.

The rate of the stimulation pulses produced by the circuit 10 is limited by the pulse rate limiter 15. The pulse rate limiting circuit 15 includes a monostable multivibrator 160 which is triggered by a trailing edge of the output pulse from the monostable multivibrator 28. The monostable multivibrator 160 includes a capacitor 161 and a resistor 162 connected respectively between its C and R terminals and its RC-terminal. The output is taken from the Q terminal, and is connected to an input of the NOR gate 30. In operation, the Q output of the monstable multivibrator 160 switches to a high state for a time determined by the time constant of the capacitor 161 and the resistor 162. During this high state, no additional pulses are permitted to pass the NOR gate 30. This disabling condition can be established at an upper desirable stimulation pulse rate, for example, 125 pulses per minute. If the output from the counter 27 should exceed this predetermined high pulse limit rate, the pulses will not be permitted to pass the NOR gate 30. Such condition, although not ordinarily possible, may result, for example, by circuit components drifts, especially after significant component aging, or the like.

The power supply for the pacer circuit 10 can be of any conveniently available type, although, because of the use of CMOS type integrated circuits, the pacer circuit 10 is particularly suitable for use with low voltage long life power supply sources, such a lithium iodide batteries or the like. As shown, two batteries 150 and 151 are provided. The batteries are connected in series, the positive terminal of the first battery 150 being connected to ground and the negative terminal of the second battery 151 being connected to a switch 153 to provide an on-off capability to the circuit 10. The switch 153 is ganged to the pulse width selection switch 40, as shown, and, in its operative position, supplies a negative potential for utilization by the circuit, as shown.

Illustrative of the particular circuit components, without limitation thereto, the realization of the pacer circuit 10 can be as follows:

| Integrated Circuits | |
|---|---|
| (RCA type) | |
| Component Number | Type |
| 27, 100 | CD 4060 |
| 90 | CD 4007 |
| 23, 160 | CD 4047 |
| 70 | CA 3078 |
| 104, 110, 43, 44, 29, 30, 123, 122 | CD 4001 |

| Resistors | |
|---|---|
| Number | Value |
| 25, 53, 65 | 1 megohm (variable) |
| 61, 73 | 30 kilohms |
| 66, 140 | 10 kilohms |
| 82 | 2 megohms (variable) |
| 50, 56, 83, 84, 128 | 1 megohm |
| 81 | 10 megohm |
| 75, 37 | 22 kilohms |
| 74 | 6.8 megohms |
| 95 | 3.9 megohms |
| 112 | 100 kilohms |
| 26 | 110 kilohms |
| 35 | 43 kilohms |
| 36 | 33 kilohms |
| 38 | 12 kilohms |
| 55 | 15 kilohms |
| 126 | 1.5 megohm |
| 137 | 1 kilohm |
| 57 | 4.7 kolohms |
| 162 | 820 kilohms |

| Capacitors | |
|---|---|
| Number | Value |
| 67, 76 | 0.33 microfarads |
| 80 | 50 picofarads |
| 111 | 0.01 microfarads |

| Capacitors | |
|---|---|
| Number | Value |

-continued

| | |
|---|---|
| 24 | 0.002 microfarads |
| 32, 125, 161 | 0.1 microfarads |
| 60 | 50 microfarads |

Diodes

| Number | Type |
|---|---|
| 19 | IN756, IN4625 |
| 72, 113 | IN3070 |
| 136 | HP5082-4655 |

Transistors

| Number | Type |
|---|---|
| 50, 51, 135 | 2N2222 |

Although the invention has been described and illustrated with a certain degree of particularity, it is understood that the present disclosure has been made by way of example only and that numerous changes in the details of construction and combination and arrangement of parts may be resorted to without departing from the spirit and scope of the invention as hereinafter claimed.

I claim:
1. A cardiac pacer for producing stimulation pulses for delivery to electrodes adapted to be connected to a heart, comprising:
   1. a stimulation pulse generator, comprising a one-shot multivibrator for producing a stimulation pulse, including:
      a. first and second gates of the type which produce an output state coinciding with selected coinciding input states, each gate having first and second inputs and an output the output of said second gate being connected to the first input of said first gate,
      b. a capacitor interconnecting the output of said first gate to the first input of said second gate, and
      c. resistor means connected to discharge said capacitor to time the width of the pulse produced by said stimulation pulse generator,
   2. a source of clock pulses,
   3. a counter connected to receive said clock pulses for applying an output state to the second input of said first gate after counting a number of said clock pulses corresponding to a stimulation pulse interval to trigger said stimulation pulse generator, and having a reset terminal connected to the output of said second gate,
   4. a monostable multivibrator having an input operative to reinitiate a timing period thereof less than the stimulation pulse interval, and having an output which changes state for said timing period after a signal is applied to the input,
      a. the input being connected to the output of said second gate,
      b. the output being connected to the second input of said second gate,
      c. whereby when said monostable multivibrator is triggered, the output thereof disables said stimulation pulse generator for the timing period thereby limiting the rate of said stimulation pulse generator to the timing period,
   5. and means for amplifying the pulse from the output of said second gate for delivery to said electrodes.
2. The cardiac pacer of claim 1 further comprising:
   means for connection to said electrodes for detecting pulses thereupon,
   a second counter connected to count clock pulses to a count of time less than said stimulation pulse interval to define a refractory period count, said second counter having an output which changes state upon reaching said refractory period count, and having a reset terminal connected to said means for detecting pulses to reinitiate the count of said second counter.
   and a capacitor connected to be charged in response to the output state of said second counter to produce a resetting of said first-mentioned counter only after said second counter has reached said refractory period count.

* * * * *